United States Patent [19]

Ghiurea

[11] 4,447,755
[45] May 8, 1984

[54] PIEZOELECTRIC TRANSDUCER ACCELEROMETER

[75] Inventor: Florin C. V. Ghiurea, Bucharest, Romania

[73] Assignee: Institutul de Cercetarea Stiintifica si Inginerie Tehnologica Pentru Industria Electrotehnica, Bucharest, Romania

[21] Appl. No.: 414,378

[22] PCT Filed: Jan. 18, 1982

[86] PCT No.: PCT/RO82/00001
  § 371 Date: Aug. 27, 1982
  § 102(e) Date: Aug. 27, 1982

[87] PCT Pub. No.: WO82/02602
  PCT Pub. Date: Aug. 5, 1982

[30] Foreign Application Priority Data
  Jan. 20, 1981 [RO] Romania ............... 103157

[51] Int. Cl.³ .............................. H01L 41/08
[52] U.S. Cl. ...................... 310/329; 73/517 R
[58] Field of Search ............. 310/328, 329, 338; 73/DIG. 4, 517 R

[56] References Cited

U.S. PATENT DOCUMENTS

| 2,411,401 | 11/1946 | Welch | 310/329 |
| 3,075,099 | 1/1963 | Shoor | 310/329 |
| 4,225,802 | 9/1980 | Suzuki et al. | 310/329 X |
| 4,359,658 | 11/1982 | Cartier | 310/329 |
| 4,373,378 | 2/1983 | Fujishiro et al. | 310/329 X |

FOREIGN PATENT DOCUMENTS 706784 12/1979 U.S.S.R. ............... 310/329

*Primary Examiner*—Mark O. Budd
*Attorney, Agent, or Firm*—Karl F. Ross; Herbert Dubno

[57] ABSTRACT

A piezoelectric transducer for use in accelerometer or vibration measurements comprises a seismic mass in the form of a casing which receives a pair of piezoelectric rings sandwiching between them a flange of a contact pin which extends axially from one end of the casing and is insulated with respect to this end by an insulating bushing. A threaded member of the casing forms one terminal of the transducer while the contact pin forms the other terminal. The rings are braced against a disk of another pin extending axially in the opposite direction from the casing and a spring is braced against this disk and a gasket threaded into the casing.

1 Claim, 1 Drawing Figure

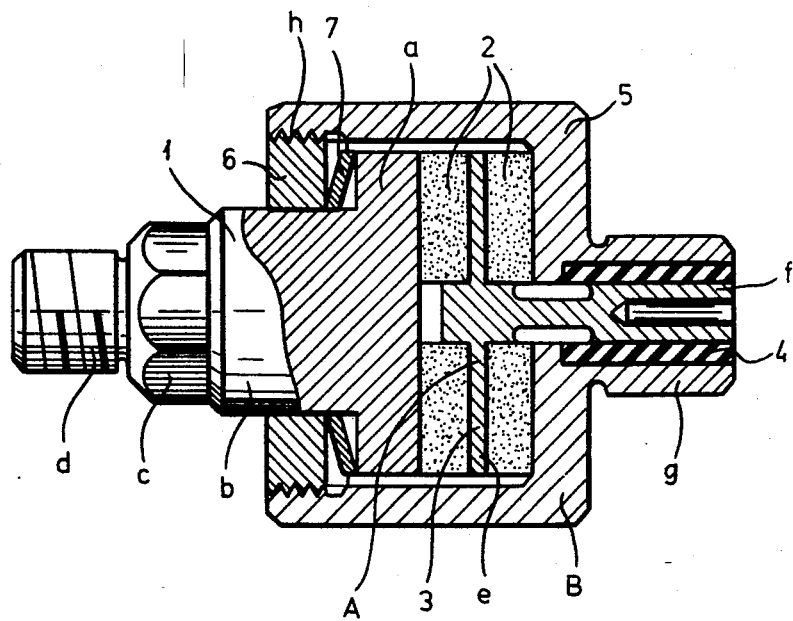

PIEZOELECTRIC TRANSDUCER ACCELEROMETER

CROSS REFERENCE TO RELATED APPLICATION

The present application is a national phase application corresponding to PCT RO-82-00001 filed Jan. 18, 1982 under the Patent Cooperation Treaty and claiming the benefit of the Romanian application No. 103,157 filed Jan. 20, 1981.

FIELD OF THE INVENTION

The invention relates to a piezoelectric transducer for an accelerometer of a type used for mechanical characteristics measurement and vibratory movement study of parts assemblies or subassemblies in operation.

BACKGROUND OF THE INVENTION

There are different constructive forms of piezoelectric axial transducers mainly having a cylindrical housing having a seismic mass inside which by its vibratory movement inertial tendency of a seismic mass to maintain the state and moving direction, exercises a pulsating pressure on a disk or on a package of piezoelectric disks, in order to transform in a linear way the pulsating impulses of the seismic mass into impulses of an electric voltage generated by a piezoelement.

These transducers show the following disadvantages:

The inactive mass, predominantly its housing, is heavier than the seismic mass (representing the active element) thus altering the vibrating movements that should be detected in the case of small-dimension parts, the vibration frequency and amplitude depending on the mass of the element in motion;

to reduce the ratio between the transducer inactive weight and its active weight (i.e. of the seismic mass). The latter is made of rare metal alloys whose price is high, like wolfram, osmium, iridium.

SUMMARY OF THE INVENTION

The piezoelectric transducer, according to this invention, eliminates the above-mentioned disadvantages, because it eliminates the adverse effect upon the vibrations to be detected by increasing the weight of the parts that are in vibration with inactive parasitic masses.

The cylindrical housing is provided at one end with a threaded section. The seismic mass which is the active element comprises a suspension disk having a sensing element made of two piezoelectric rings assembled with parts of the same polarity mounted towards an intermediary disk of a contact bolt, fixed by an isolating sleeve in the housing of the transducer.

BRIEF DESCRIPTION OF THE DRAWING

The sole FIGURE is a longitudinal section of a transducer according to the invention.

SPECIFIC DESCRIPTION

The piezoelectric transducer comprises a contact pin 1, formed with a disk a, braced by a connecting cylinder b, continued by a key hexagon c, provided with a threaded section d, being the purpose of fixing the transducer on the part (not shown) whose vibrations should be detected.

The suspension disk a of the pin 1 has one or more sensing elements A, made of a pair of piezoelectric rings 2 arranged with the faces of the same polarity on an intermediary disk e of a contact pin 3, provided with a terminal section f, which constitutes one of the two poles of the transducer.

The pin 3 is surrounded by an insulating sleeve 4 enclosed in the seismic mass B, having a threaded section g, which can be taken as the other pole and allows transducer connection for transmitting impulses generated by the piezoelectric rings 2.

At the opposite end, the cylindrical part 5 of the seismic mass B, is provided with an inner thread h, into which a gasket cover 6 is screwed engaging the contact pin 1.

Inside the casing, having the role of a seismic mass B, there is a prestressed spring disk 7 bracing disk A of the contact pin 1 against the seismic mass B.

The piezoelectric transducer, according to this invention has the following advantages:

simple construction, at low cost, with increased performances;

its weight is the weight of the seismic mass, which is the active element, avoiding degradation of the vibrations to be detected;

allows fabrication of piezoelectric transducers of the accelerometer type, with increased efficiency, without the use of costly alloys of rare metals with high density like tungsten, iridium, osmium.

I claim:

1. A piezoelectric transducer for accelerometer and vibration measurement studies which comprises:
   a cylindrical casing forming a seismic mass and formed with an internal thread at one end and an axially extending externally threaded tubular stem at an opposite end, said stem forming one pole for electrical connection to the transducer;
   a pin extending from said one end of said casing axially and formed within said casing with a disk, a face of said disk confronting a face of said casing at said other end but spaced therefrom;
   a pair of piezoelectric rings respectively abutting said faces and having parts of the same polarity turned toward one another;
   a contact bolt extending axially from said other end of said casing, insulated relative to said other end of said casing by an insulating bushing, and formed within said casing with an annular flange disposed between the parts of the same polarity whereby said contact bolt forms a second pole for electrical connection to the transducer;
   a gasket threaded into said casing at said one end, said pin extending through said gasket; and
   a spring member braced against said gasket and urging said disk against said rings.

* * * * *